(12) United States Patent
James (10) Patent No.: US 8,553,840 B2
(45) Date of Patent: Oct. 8, 2013

(54) BIOMETRIC DIAGNOSIS

(75) Inventor: Veronica James, Queensland (AU)

(73) Assignee: Veronica James Consulting Pty Ltd, Robina Qld (AU)

( * ) Notice: Subject to any disclaimer, the term of this patent is extended or adjusted under 35 U.S.C. 154(b) by 0 days.

(21) Appl. No.: 13/533,327

(22) Filed: Jun. 26, 2012

(65) Prior Publication Data

US 2013/0077753 A1    Mar. 28, 2013

Related U.S. Application Data (63) Continuation of application No. 12/520,740, filed as application No. PCT/AU2008/000005 on Jan. 3, 2008, now abandoned.

(30) Foreign Application Priority Data

Jan. 12, 2007  (AU) .............................. 2007900131
Jul. 9, 2007   (AU) .............................. 2007903706

(51) Int. Cl.
    *G01N 23/20*    (2006.01)
(52) U.S. Cl.
    USPC ............................................... 378/71; 378/70
(58) Field of Classification Search
    USPC ............................. 378/70, 71, 82, 83, 86–88
    See application file for complete search history.

(56) References Cited

U.S. PATENT DOCUMENTS 6,718,007 B1 *  4/2004  James ............................. 378/70

* cited by examiner

*Primary Examiner* — Anastasia Midkiff (57) ABSTRACT

The invention provides a method of detecting neoplastic or neurological disorders comprising exposing skin or nails to X-ray diffraction and detecting changes in the ultrastructure of the skin or nails, and also provides an instrument when used in the method of detection.

4 Claims, 9 Drawing Sheets

BIOMETRIC DIAGNOSIS

RELATED APPLICATIONS

This application is a Continuation Application of U.S. patent application Ser. No. 12/520,740, filed 6 Jan. 2010, now abandoned which is a U.S. National Phase Application of International Application No. PCT/AU2008/000005, filed 3 Jan. 2008, which claims the benefit of Australian Patent Application No. 2007900131, filed 12 Jan. 2007 and Australian Patent Application No. 2007903706, filed 9 Jul. 2007, all of which are incorporated herein by reference in their entirety.

TECHNICAL FIELD

The invention described herein relates generally to a biometric diagnostic method. In particular, the invention is directed to the use of skin or nails to detect neoplastic or neurological disorders, although the scope of the invention is not necessarily limited thereto.

BACKGROUND ART

There is at present no completely reliable, non-invasive test for neurological and neoplastic disorders. Whilst specific changes in the diffraction patterns of hair have been established for breast and colon cancers and Alzheimer's disease (WO 00/34774), this test has complications resulting from cosmetic hair treatments such as dyes, back-combing and even brushing and by transportation through security X-rays either at airports or in the post. In addition, many neoplastic and neurological disorders do not cause a change in the ultrastructure of hair, and therefore this test is very limited, for example prostate cancer and melanoma, even at Grade 7, do not show any changes in the structure of hair.

Therefore, there would be an advantage if it were possible to provide an alternative test for many of these conditions which may overcome at least some of the above-mentioned disadvantages or provide a useful or commercial choice.

SUMMARY OF THE INVENTION

The invention describes a test which provides early, low cost, totally non-invasive yet reliable tests, which could possibly be low-cost mass screening for neurological and neoplastic disorders, using samples of biological material which can be harvested at remote locations, which samples do not deteriorate with correct storage.

In a first embodiment, the invention provides a method of detecting neoplastic or neurological disorders in a subject, the method comprising exposing biological material of the subject to fibre X-ray diffraction, and detecting changes in the ultrastructure of the biological material, wherein the biological material is a skin or nail sample, and wherein when the biological material is a skin sample, the neoplastic disorder is not BRCA1-related breast cancer.

In a second embodiment, the invention provides an instrument when used in the method of the first embodiment, the instrument comprising: an X-ray source producing a beam of X-radiation; a sample stage for positioning the biological sample within the beam; a detector for detecting scattering of the X-ray beam; and a display means associated with the detector for displaying the output of the detector, whereby diffraction patterns of related output are displayed for interpretation.

With regard to the first and second embodiments as defined above, when the biological material is a skin sample, the neoplastic disorder can be any disorder which causes a measurable change in the ultrastructure of the sample. The method is particularly accurate for detecting the presence of prostate cancer and melanoma in a subject, using a skin sample.

When the biological material is a nail sample, the neoplastic disorder can be any disorder which causes a measurable change in the ultrastructure of the sample. The method is particularly accurate for detecting the presence of breast and colon cancers in a subject, using a nail sample.

When the biological material is a nail sample, the neurological disorder can be any disorder which causes a measurable change in the ultrastructure of the sample. The method is particularly accurate for detecting the presence of Alzheimer's disease in a subject.

The skin and nail samples can be obtained by any practicable means. Preferably skin biopsy samples are obtained by routine methods and are placed immediately in pathological saline and stored at $-20°$ C. until required. The samples can be mounted to the sample stage in any practicable manner. Preferably the skin samples are mounted using sutures attached to the sides, stretched slightly to remove the crimp, in cells specially designed to maintain 100% humidity. An analysis of the resulting films enables the presence of prostate cancer or melanoma to be determined.

Preferably nail samples are cut from nail clippings. The sample size is preferably about 1 mm square to enable the X-ray beam to fit entirely within the sample. Preferably, the nail samples have minimal curvature over the length.

The samples can then be mounted on the ends of microtubules and exposed to finely focused X-ray beams of sufficient intensity, such as those from fixed tube, fine-focus generators, rotating-anode generators and synchrotron sources. An analysis of the resulting films enables the presence of the pathological states to be determined.

The X-ray source used in the invention can be any appropriate X-ray source, but preferably must produce monochromatic X-rays within the energy range of 5 to 30 keV. Radiation from synchrotron sources is well suited for this work but radiation from rotating anode generators and fine focussed X-ray sources can also be used with appropriately longer exposure times.

The X-ray diffraction is preferably carried out using a monochromatic X-ray source facility such as a low angle synchrotron facility, for example BL15A, Photon Factory, Tsukuba with an X-ray wavelength between 0.06 and 0.20 nm. An incident flux at the specimen of approximately $8 \times 10^{10}$ photons per sec can be generated when the Photon Factory storage ring is operated at 25 GeV with a beam current of 145 mA. The X-ray patterns can be recorded on Fuji BAS III Imaging plates.

Exposure time for the skin samples can be any time long enough to obtain meaningful results, but is preferably between 20 s and 5 minutes. At $3^{rd}$ generation synchrotrons such as the Advanced Photon Source (APS), Argonne USA the exposure time is reduced to 1 to 10 s. An exposure time on rotating generators and fine focused X-ray generators is typically 15 minutes to 24 hours.

Sample to imaging plate distances can be any practicable distance, but are preferably 200 mm to 3000 mm. 1000 mm is common on BioCAT, APS, 800 mm on ChemMatCARS (APS), 400 mm on BL15A (Photon Factory) and 200 mm on rotating anodes.

Background removal can be achieved by use of standard packages such as FIT2D, MATHEMATICA and IRAFSAO.

The meridional data can be analyzed using a Bragg analysis; the equatorial data can be analyzed using appropriate Bessel Functions.

In order that the invention may be more readily understood and put into practice, one or more preferred embodiments thereof will now be described, by way of example only, with reference to the accompanying drawings.

DETAILED DESCRIPTION OF PREFERRED EMBODIMENTS

Fibre diffraction requires samples containing numerous fibres which are arranged in a regular array of parallel planes. The greater the number of planes, the better will be the final patterns obtained.

At the microscopic level, skin is comprised of three layers. Of these the dermis is the middle layer and is also the thickest of the three layers (1.5 to 4 mm thick), making up approximately 90% of the thickness of the skin. The dermis is held together by a protein called collagen which is a tough, insoluble protein found throughout the connective tissues of the body. The lower, reticular layer of the dermis is thicker and made of thick collagen fibres that are aligned parallel to the surface of the skin, making it ideal for fibre diffraction.

Anatomically fingernails and toenails are made of hard α-keratin and are produced from living skin cells in the fingers and toes as a hard, curved plate. The free edge is the part of the nail that extends past the finger or toe, beyond the nail plate. The α-keratin fibres are arranged parallel to the free edge. This makes nails suitable for diffraction work.

Since the basic repeat distances in skin collagen (65.2 nm) and keratin (46.7 nm and 62.6 nm) are very large on the atomic scale and the diffraction angles are reciprocal, low angle x-ray diffraction is required to achieve excellent scattering results. However the fundamental structures of both collagen and keratin have been determined using this technology. The patterns are eminently reproducible from tissue to tissue and from sample to sample. The specific changes observed in skin collagen and in nail keratin for neoplastic and neurological disorders are also clearly reproducible and quite specific to the particular pathology.

Figure 1:
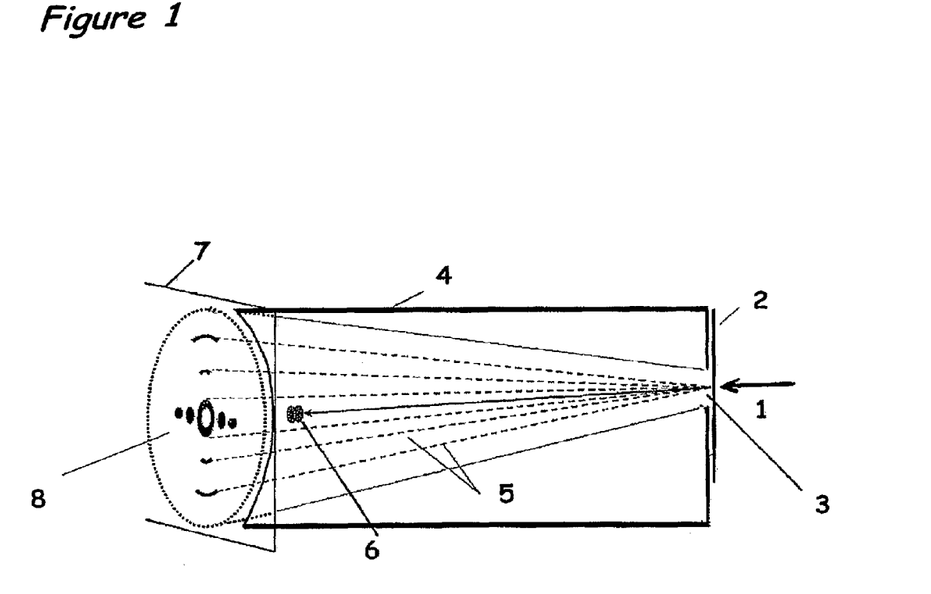
FIG. 1 is a schematic representation of the X-ray analysis system of the invention.

FIG. 1 depicts a system for analyzing fibres according to the present invention.

Figure 2:
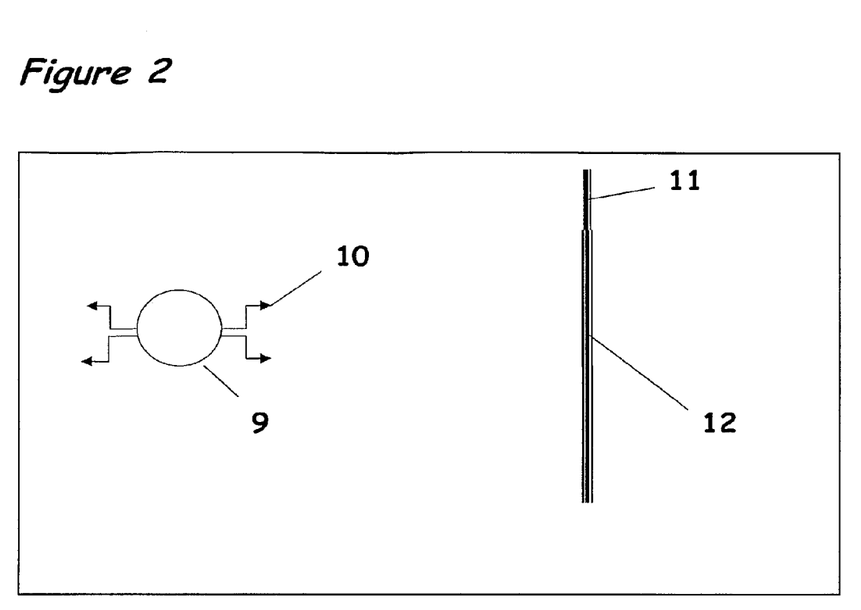
FIG. 2 is a schematic representation of sample mounting arrangements.

Samples for analysis are prepared as described below (FIG. 2). Analysis of the samples is as follows (FIG. 1). A finely focussed collimated monochromatic x-ray beam (1) is diffracted from the sample (2), and passes through the window (3) of an evacuated flight tube (4), and exits through a window at the other end of the flight tube as diffracted rays (5), to reach the detecting device (7). The beam (1) is centered within the sample (2) and small enough to fit entirely within the sample.

The direct beam is very strong and would damage the detector. The direct beam is therefore intercepted by a beamstop (6), which allows the much weaker diffracted beam to reach and be focussed at the imaging plate or detector (7). The path between the sample (2) and the detecting device (image plate) (7) is evacuated to prevent loss of intensity by scatter from the atmosphere.

Sample (2) to imaging plate (7) distances are as described above.

The X-ray patterns (8) are recorded on both Fuji BasIII Imaging plates and also on electronic detectors. Exposure time for the skin and for nail samples depends on sample and beam-line but varies from 5 seconds to 20 minutes.

Background removal is achieved by use of the two astronomy packages IRAF and SAO, and checked by using SAX15ID or a combination of MATLAB and ProcessFITS. The meridional data is analyzed using a Bragg analysis, and the equatorial data analyzed using appropriate Bessel Functions.

Samples are prepared in the following manner (FIG. 2).

Small punch biopsy samples of skin (9) are attached by sutures (10) and mounted in cells which can maintain 100% humidity throughout exposure to the X-ray beam.

Small "crystallite" sections of nails (11) (approximately 1×2 mm in size) are cut from nail clippings and mounted on the ends of microtubules (12). These microtubules are then firmly held in place on a grooved plate.

Figure 3:
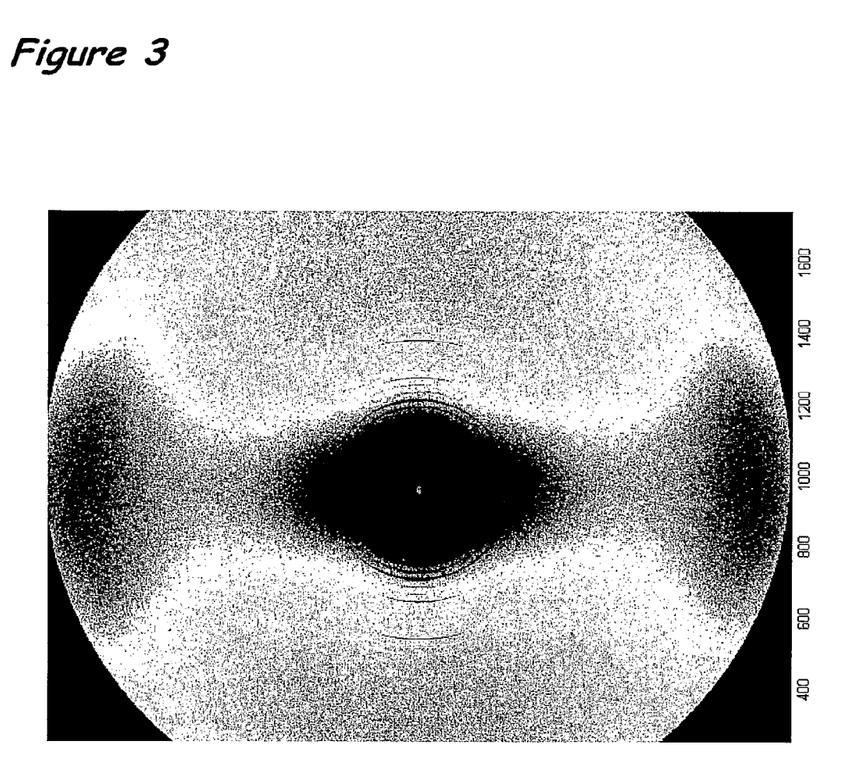
FIG. 3 is an X-ray diffraction pattern obtained from skin of a healthy subject.
Figure 6:
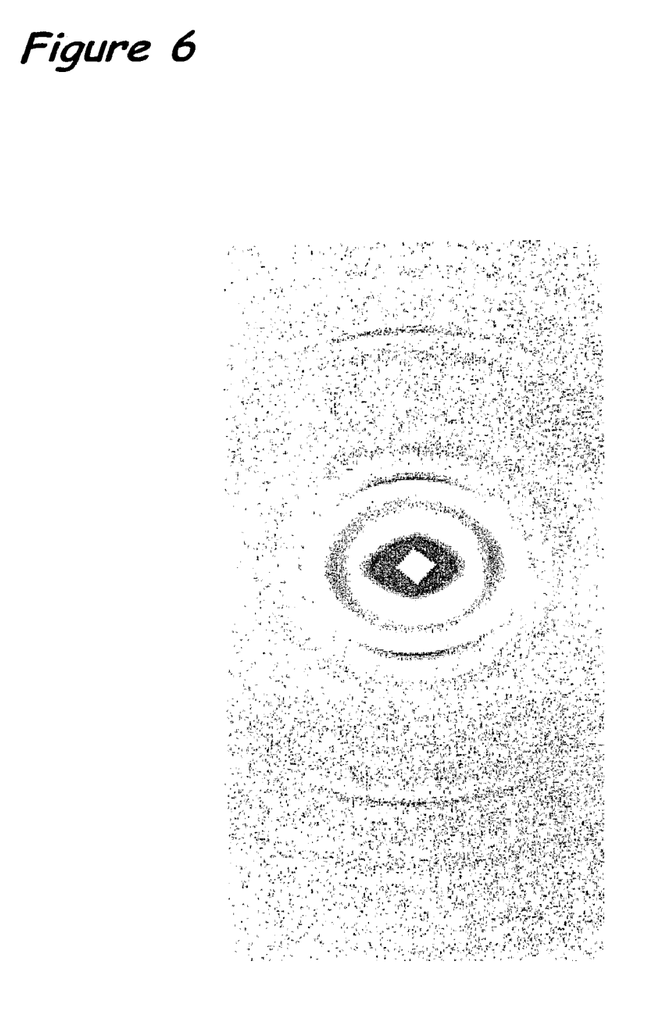
FIG. 6 is an X-ray diffraction pattern obtained from nail of a healthy subject.

The inventor has found that normal skin and nails of all post-partum persons so examined yielded distinctive repeatable patterns which varied only slightly over the age range from 3 months to 80 years. A typical synchrotron pattern for normal skin is given in FIG. 3 and that for normal nails is given in FIG. 6. The meridional pattern (vertical) arises from repeat collagen helical lattice in the direction of stretch of the skin sample or from the helical arrangements of keratin in the nails, the samples being mounted in the longer direction of the beam. The equatorial pattern (horizontal) reflects the cylindrical packing arrangement of the intermediate filaments perpendicular to the beam.

Figure 4:
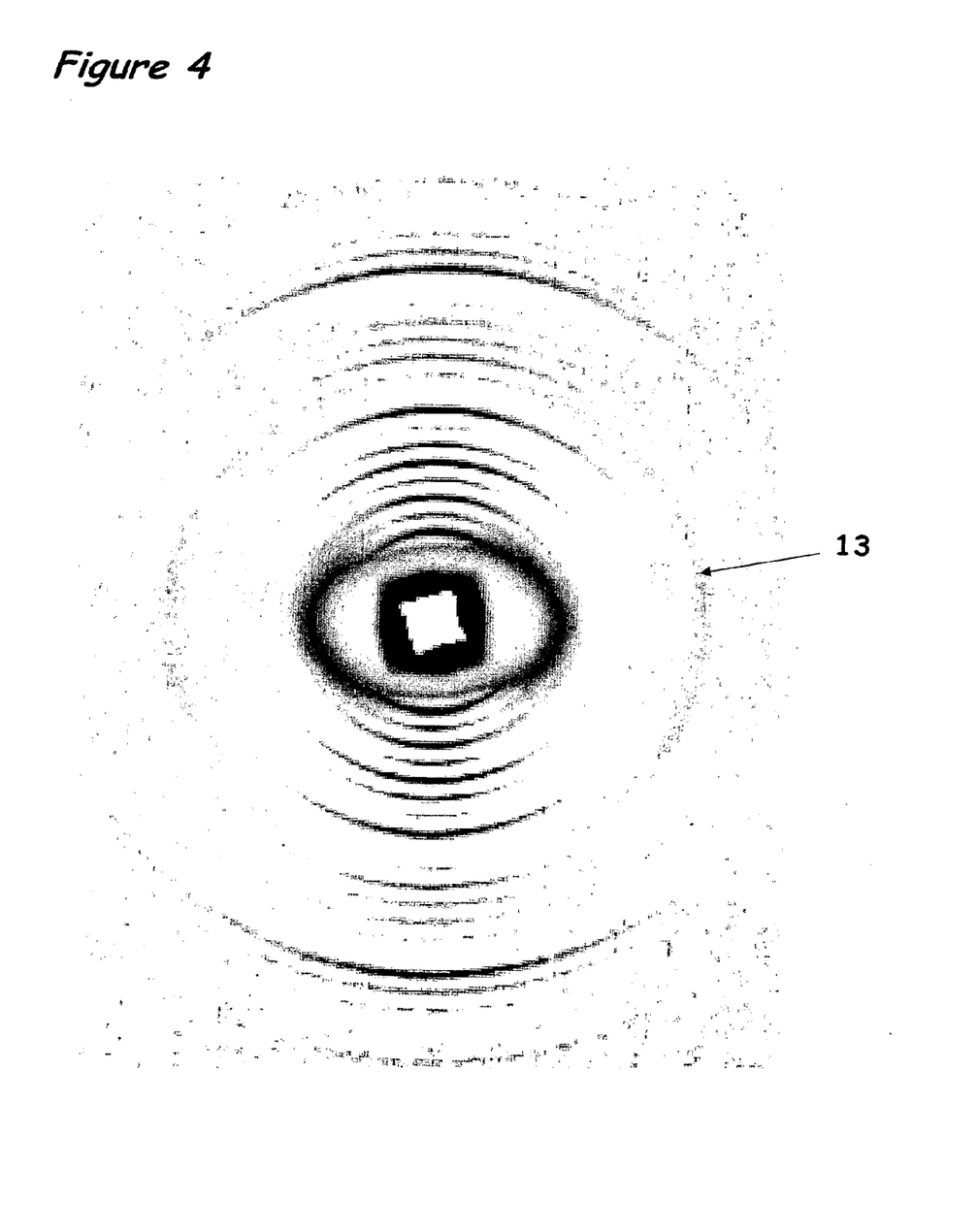
FIG. 4 is an X-ray diffraction pattern obtained from the skin of a patient with prostate cancer.
Figure 5:
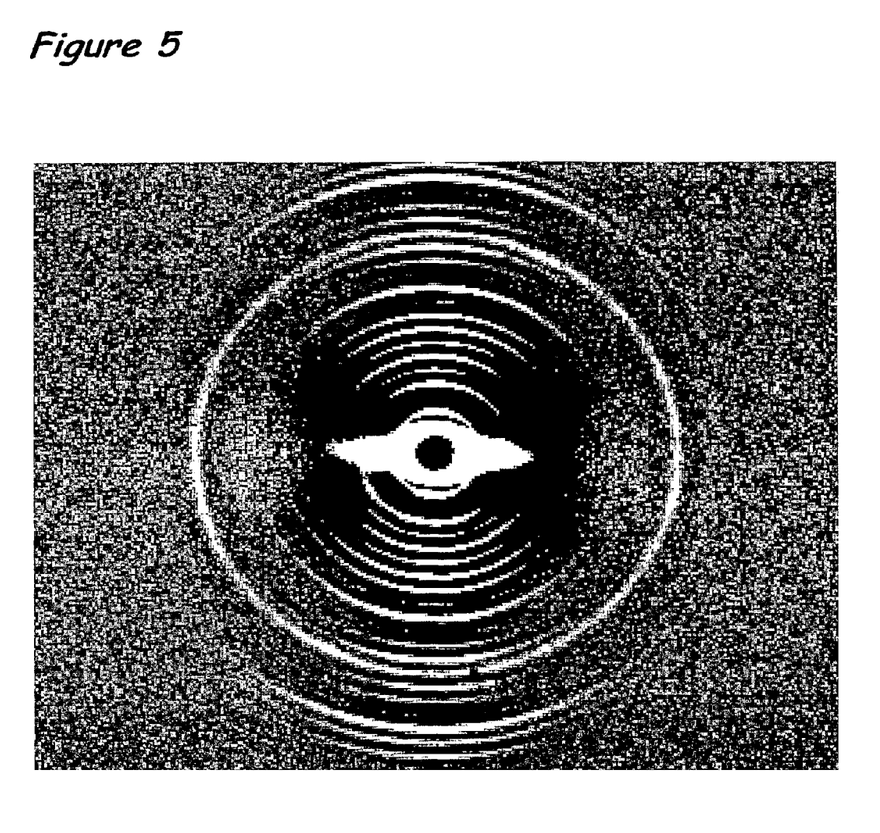
FIG. 5 is an X-ray diffraction pattern obtained from the skin of a patient with melanoma.
Figure 7:
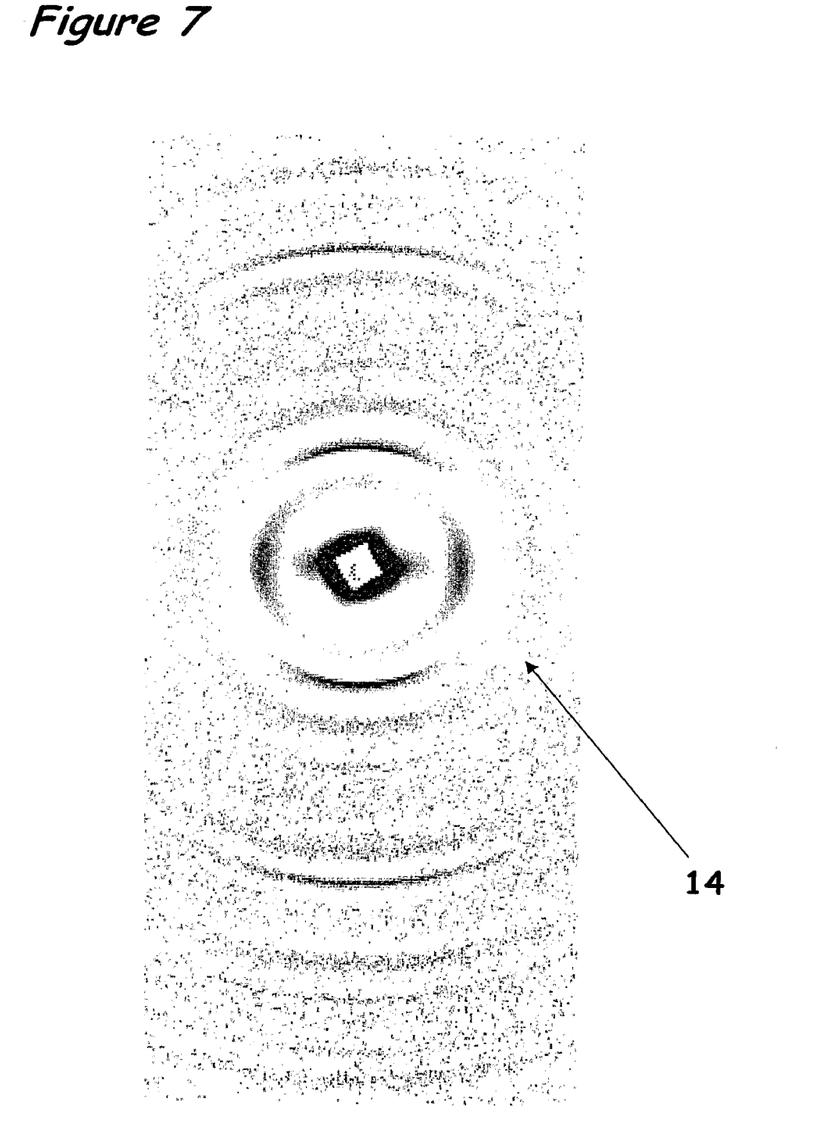
FIG. 7 is an X-ray diffraction pattern obtained from the nail of a patient with nonBRCA1-related breast cancer.
Figure 8:
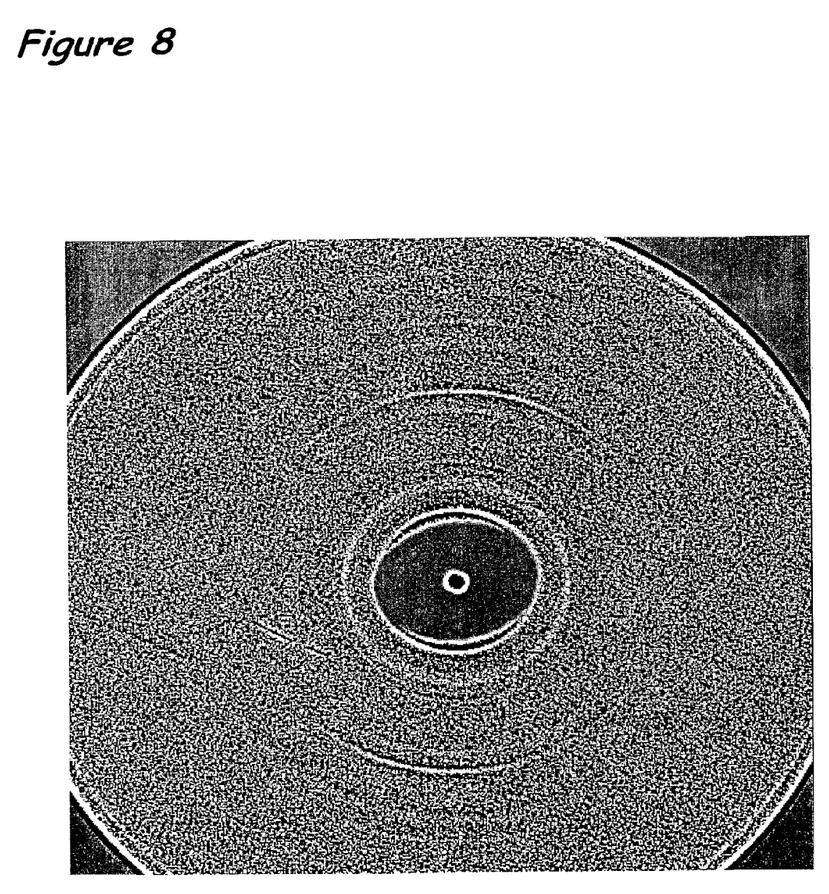
FIG. 8 is an X-ray diffraction pattern obtained from the nail of a patient with colon cancer.
Figure 9:
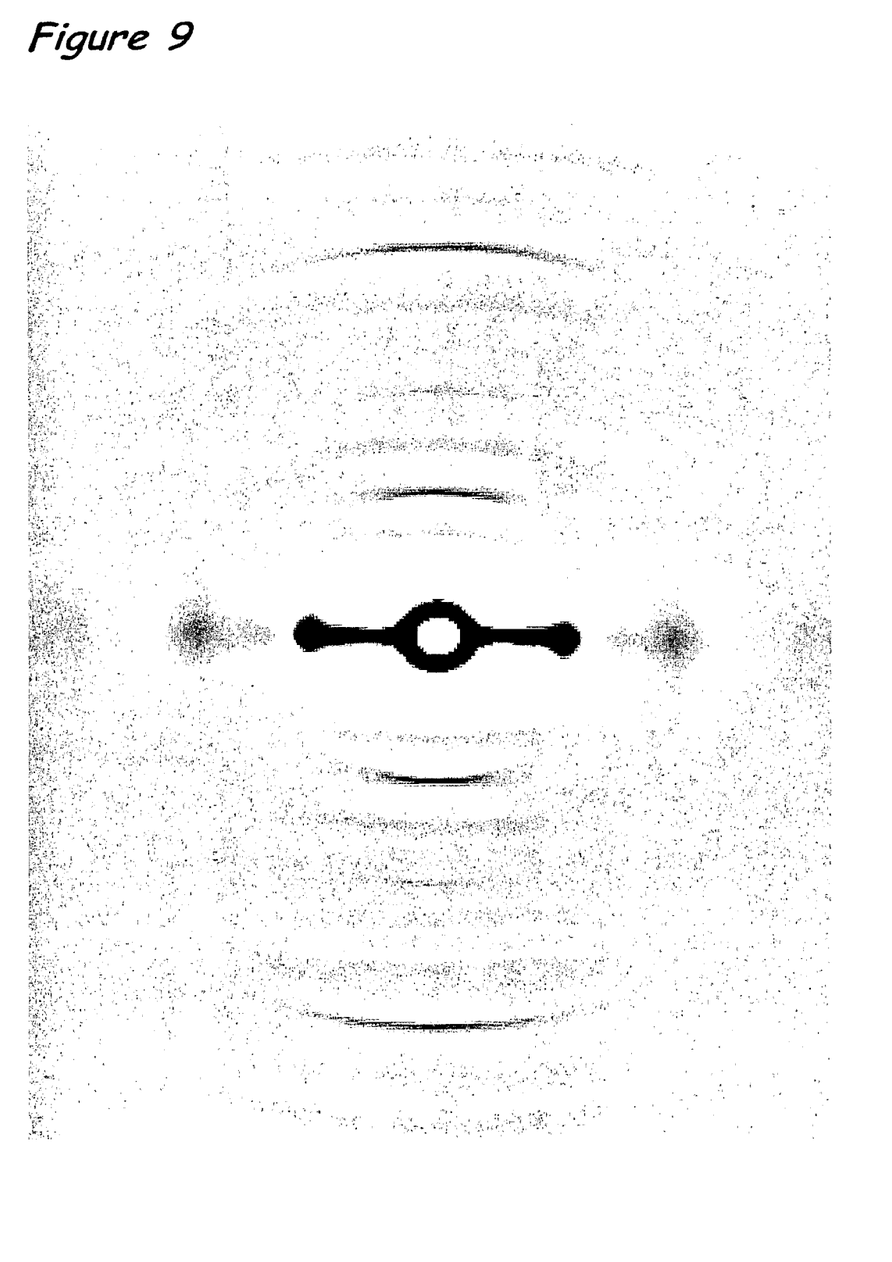
FIG. 9 is an X-ray diffraction pattern obtained from the nail of a patient with Alzheimer's disease.

Further sets of samples included:
1) Skin biopsies from:
 (a) patients known to have prostate cancer. Specific change observed for diffraction patterns (13) from all such patients is shown in FIG. 4.
 (b) patients known to have melanoma. Specific change observed for diffraction patterns from all such patients is shown in FIG. 5.
2) Finger and toenails from:
 (a) patients known to have breast cancer. Specific change observed for diffraction patterns (14) from all such patients is shown in FIG. 7.
 (b) patients known to have colon cancer. Specific change observed for diffraction patterns from all such patients is shown in FIG. 8.
 (c) patients known to have Alzheimer's disease. Specific change observed for diffraction patterns from all such patients is shown in FIG. 9.

The changes observed manifested in samples taken from the relevant groups of patients. For patients with prostate cancer and melanoma the relevant changes consisted of rings of different diameters superimposed on the normal pattern for skin collagen. Based on the accepted D-spacing for wet skin of 65.2±0.5 nm, the relative spacing of the additional rings in real space is 4.72±0.05 nm for prostate cancer and 4.08 nm for melanoma.

For patients with breast cancer and colon cancer the relevant changes consisted of rings of different diameters superimposed on the normal pattern for nail. Based on the accepted α-keratin D-spacing of 46.7±0.3 nm, obtained from the 91$^{st}$ order of this lattice and using the first order only of the relevant extra ring, the relative spacing of the additional rings in real space is 4.71±0.05 nm for breast cancer and 4.53 nm for colon cancer and for Alzheimer's disease an additional equatorial cone of intensity superimposed on the normal keratin pattern for nail.

Although the number of samples investigated thus far is in total over 250, the reproducibility of the results is good. The flexibility of this technique and the fact that, when using synchrotron sources, each sample takes only seconds to measure and only minutes to interpret, makes it an attractive tool for rapid and accurate diagnosis of neoplastic and neurological disorders.

It should be clear that the present invention will find wide applicability in the medical and veterinary fields, particularly in the area devoted to detecting the propensity of a subject to neoplastic and neurological disorders, including prostate cancer, colon cancer, melanoma, breast cancer and Alzheimer's disease.

The foregoing embodiments are illustrative only of the principles of the invention, and various modifications and changes will readily occur to those skilled in the art. The invention is capable of being practiced and carried out in various ways and in other embodiments. It is also to be understood that the terminology employed herein is for the purpose of description and should not be regarded as limiting.

The term "comprise" and variants of the term such as "comprises" or "comprising" are used herein to denote the inclusion of a stated integer or stated integers but not to exclude any other integer or any other integers, unless in the context or usage an exclusive interpretation of the term is required.

Any reference to publications cited in this specification is not an admission that the disclosures constitute common general knowledge in Australia.

The claims defining the invention are as follows:

1. A method of detecting neoplastic disorders in a subject, the method comprising exposing a skin sample of the subject to fiber x-ray diffraction, and detecting changes in the ultra-structure of the skin wherein the neoplastic disorder is prostate cancer or melanoma.

2. A method of detecting neoplastic or neurological disorders in a subject, the method comprising exposing a fingernail sample of the subject to fiber x-ray diffraction, and detecting changes in the ultra-structure of the fingernail wherein the neoplastic disorder is one or more of breast cancer and colon cancer and the neurological disorder is Alzheimer's disease.

3. The method of one of claim 1 or 2, wherein the x-rays are derived from an x-ray source with energies between 5 and 25 keV and wavelengths between 0.06 and 0.20 nm.

4. The method of claim 2, wherein the source is a low-angle synchrotron facility.

\* \* \* \* \*